United States Patent
Oz et al.

(10) Patent No.: US 9,763,583 B2
(45) Date of Patent: Sep. 19, 2017

(54) ELECTRODES FOR ABDOMINAL FETAL ELECTROCARDIOGRAM DETECTION

(71) Applicant: Nuvo Group Ltd., Tel Aviv (IL)

(72) Inventors: Oren Oz, Modiin (IL); Muhammad Mhajna, Tel Aviv (IL); Nathan Intrator, Tel Aviv (IL)

(73) Assignee: Nuvo Group Ltd., Ramat Gan (IL)

(*) Notice: Subject to any disclaimer, the term of this patent is extended or adjusted under 35 U.S.C. 154(b) by 0 days.

(21) Appl. No.: 15/071,956

(22) Filed: Mar. 16, 2016

(65) Prior Publication Data

US 2016/0270675 A1    Sep. 22, 2016

Related U.S. Application Data

(63) Continuation-in-part of application No. 14/921,489, filed on Oct. 23, 2015, now Pat. No. 9,392,952.

(60) Provisional application No. 62/133,485, filed on Mar. 16, 2015.

(51) Int. Cl.
*A61B 5/024*    (2006.01)
*A61B 5/0444*    (2006.01)
*A61B 5/00*    (2006.01)
*A61B 5/04*    (2006.01)

(52) U.S. Cl.
CPC ........ *A61B 5/02411* (2013.01); *A61B 5/0444* (2013.01); *A61B 5/4362* (2013.01); *A61B 5/6823* (2013.01); *A61B 5/04012* (2013.01)

(58) Field of Classification Search
CPC . A61B 5/02411; A61B 5/0444; A61B 5/4362; A61B 5/6823; A61B 5/04012
See application file for complete search history.

(56) References Cited

U.S. PATENT DOCUMENTS

| | | | | |
|---|---|---|---|---|
| 4,771,783 A * | 9/1988 | Roberts | ............... | A61B 5/0416 600/392 |
| 4,781,200 A * | 11/1988 | Baker | ............... | A61B 5/02411 600/483 |
| 5,749,831 A * | 5/1998 | Baker | ............... | A61B 8/02 600/301 |
| 7,769,473 B2 * | 8/2010 | Axelgaard | ............ | A61N 1/0452 600/372 |
| 8,892,181 B2 * | 11/2014 | Wolfberg | ............. | A61B 5/0444 600/391 |
| 2005/0267377 A1 * | 12/2005 | Marossero | ......... | A61B 5/02411 600/511 |
| 2011/0306862 A1 * | 12/2011 | Hayes-Gill | ........ | A61B 5/04085 600/382 |
| 2017/0105646 A1 * | 4/2017 | Bryenton | ............. | A61B 5/6828 |

* cited by examiner

*Primary Examiner* — Catherine Voorhees
(74) *Attorney, Agent, or Firm* — Greenberg Traurig LLP

(57) ABSTRACT

The invention provides systems and methods for monitoring the wellbeing of a fetus by the non-invasive detection and analysis of fetal cardiac electrical activity data.

14 Claims, 14 Drawing Sheets

Section A-A

ELECTRODES FOR ABDOMINAL FETAL ELECTROCARDIOGRAM DETECTION

CROSS REFERENCE TO RELATED APPLICATIONS

This application claims priority to U.S. Provisional Patent Application No. 62/133,485, filed on Mar. 16, 2015, and U.S. patent application Ser. No. 14/921,489, filed on Oct. 23, 2015, the entire contents of which are incorporated by reference in their entirety.

FIELD OF THE INVENTION

The invention relates generally to electrodes suitable for use in fetal heart rate monitoring systems.

BACKGROUND

Monitoring fetal cardiac electrical activity can be useful to determine of the health of a fetus during pregnancy.

SUMMARY

In one embodiment, the present invention provides an electrode configured to detect fetal electrocardiogram signals, comprising:
a) a cutaneous contact for sensing fetal electrocardiogram signals from a pregnant human subject;
b) a connector in electrical contact with the cutaneous contact for connection to a lead wire; and
c) a substructure for attachment to a human pregnant subject,
   wherein, the cutaneous contact is configured on the substructure to allow a surface of the cutaneous contact to be in electrical communication with the skin of the pregnant human subject.

In one embodiment, the cutaneous contact is configured to have skin-electrode impedance of greater than 150 k$\Omega$.
In one embodiment, the cutaneous contact is configured to have skin-electrode impedance of less than 150 k$\Omega$.
In one embodiment, the cutaneous contact is configured to have skin-electrode impedance of between 5 to 150 k$\Omega$.
In one embodiment, the cutaneous contact is attached to an elastomeric structure that is configured to deform when placed on the abdomen of the pregnant human subject to create a skin-electrode impedance of less than 150 k$\Omega$.
In one embodiment, the cutaneous contact is attached to an elastomeric structure that is configured to deform when placed on the abdomen of the pregnant human subject to create a skin-electrode impedance of between 5 to 150 k$\Omega$.
In one embodiment, the cutaneous contact is configured to have a surface resistance of less than 1 $\Omega$/square.
In one embodiment, the cutaneous contact is configured to have a surface resistance between 0.01 and 1 $\Omega$/square.
In one embodiment, the signal to noise ratio of the fetal electrocardiogram signals is between −20 dB and 50 dB.
In one embodiment, the signal to noise ratio of the fetal electrocardiogram signals is between 0 dB and 50 dB.
In one embodiment, the signal to noise ratio of the fetal electrocardiogram signals is less than 50 dB.
In one embodiment, the cutaneous contact is an electrically conductive fabric.
In one embodiment, the electrically conductive fabric has a skin-electrode impedance of less than 150 k$\Omega$.
In one embodiment, the electrically conductive fabric has a skin-electrode impedance of between 5 to 150 k$\Omega$.
In one embodiment, the surface of the electrically conductive fabric that forms the cutaneous contact is configured to have a surface resistance of less than 1 $\Omega$/square.

In one embodiment, the present invention provides a garment, comprising:
at least one pair of electrodes,
   wherein the at least one pair of electrodes are configured, when the garment is worn by the pregnant human subject, such that the individual electrodes of the at least one electrode pair encircle the uterus of the pregnant human subject, and
   wherein the individual electrodes of the at least one electrode pair comprise:
      a) a cutaneous contact for sensing fetal electrocardiogram signals from a pregnant human subject;
      b) a connector in electrical contact with the cutaneous contact for connection to a lead wire; and
      c) a substructure for attachment to a human pregnant subject,
         wherein, the cutaneous contact is configured on the substructure to allow a surface of the cutaneous contact to be in electrical communication with the skin of the pregnant human subject;
      wherein cardiac electrical activity data is recorded from the at least one sensor pair.

DETAILED DESCRIPTION

For clarity of disclosure, and not by way of limitation, the detailed description of the invention is divided into the following subsections that describe or illustrate certain features, embodiments or applications of the present invention.

As used herein the term "contact region" encompasses the contact area between the skin of a pregnant human subject and cutaneous contact i.e. the surface area through which current flow can pass between the skin of the pregnant human subject and the cutaneous contact.

In some embodiments, the present invention provides a system for detecting, recording and analyzing cardiac electrical activity data from a pregnant human subject. In some embodiments, a plurality of electrodes configured to detect fetal electrocardiogram signals is used to record the cardiac activity data. In some embodiments, a plurality of electrodes configured to detect fetal electrocardiogram signals and a plurality of acoustic sensors are used to record the cardiac activity data.

In some embodiments, a plurality of electrodes configured to detect fetal electrocardiogram signals are attached to the abdomen of the pregnant human subject. In some embodiments, the plurality of electrodes configured to detect fetal electrocardiogram signals are directly attached. In some embodiments, the plurality of electrodes configured to detect fetal electrocardiogram signals are incorporated into an article, such as, for example, a belt, a patch, and the like, and the article is worn by, or placed on, the pregnant human subject.

In some embodiments, the present invention provides an electrode configured to detect fetal electrocardiogram signals, comprising:
a) a cutaneous contact for sensing fetal electrocardiogram signals from a pregnant human subject;
b) a connector in electrical contact with the cutaneous contact for connection to a lead wire; and
c) a substructure for attachment to a human pregnant subject
wherein, the cutaneous contact is configured on the substructure to allow a surface of the cutaneous contact to be in electrical communication with the skin of the pregnant human subject.

Without intending to be limited to any particular theory, in some embodiments, the three-dimensional shape of the electrode affects the performance. For example, a curved profile without sharp angles is likely to prevent abrupt changes in the electrical field generated by the cutaneous contact, or flow of current from the cutaneous contact to the lead wire.

Figure 1:
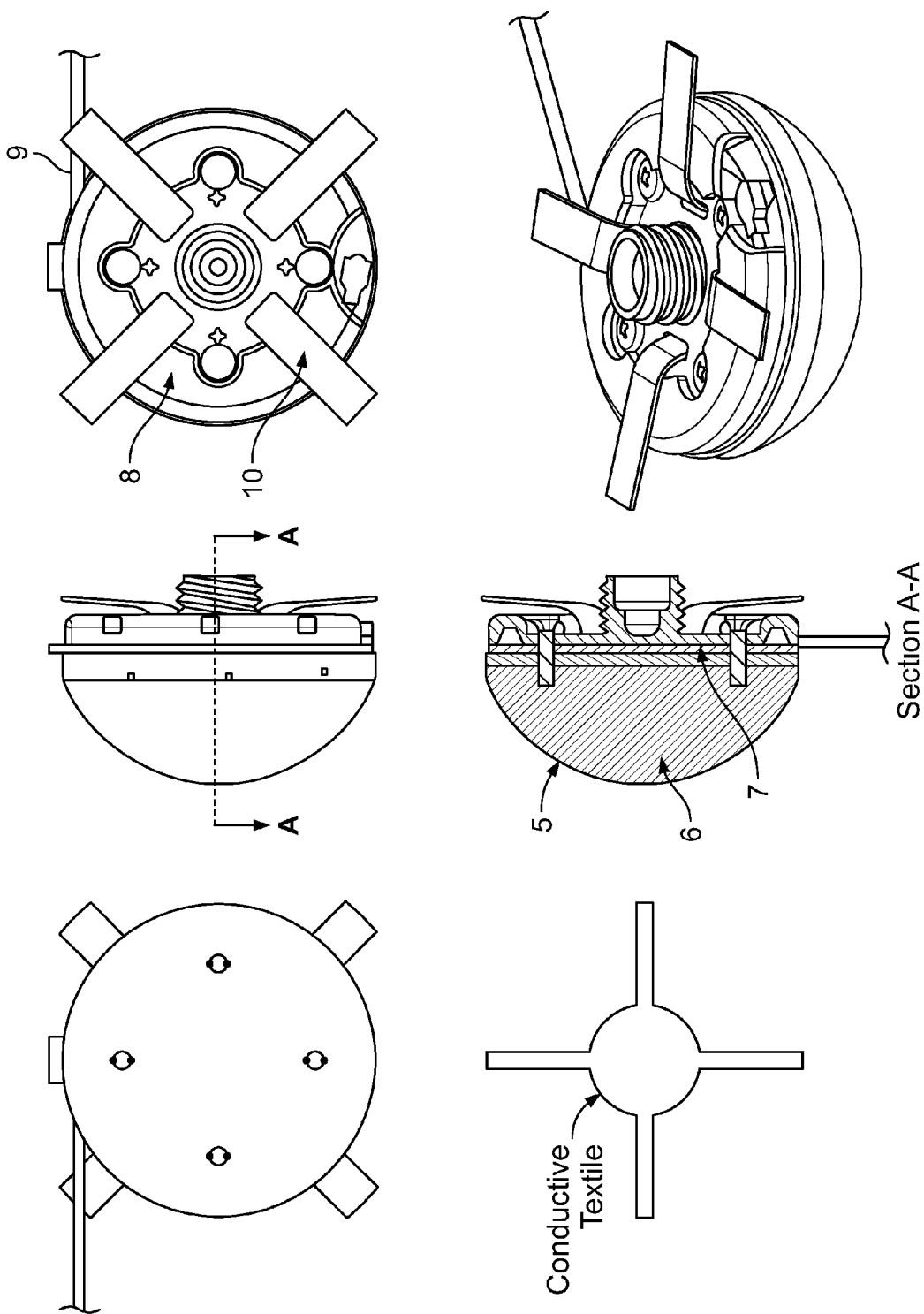
FIG. 1 shows an electrode according to some embodiments of the present invention.

FIG. 1 shows a circular electrode according to some embodiments of the present invention. In the embodiment shown in FIG. 1, the electrode, as shown along the section A-A, comprises an electrically conductive fabric (5) attached over an elastomeric dome shaped circular structure (6), which is, in turn, attached to a circular foam backing (7). The foam backing is attached to a printed circuit board (8), which has one electrical connection (9) that outputs the sensed fetal electrocardiogram signals, and at least one electrical connection (10) that connects the electrically conductive fabric to the printed circuit board (8).

In some embodiments, the printed circuit board is configured to interface the cutaneous contact with the lead wire. Alternatively, in some embodiments, the printed circuit board is further configured to perform additional functions, such as, for example, signal filtering, or pre-amplification.

Figure 2:
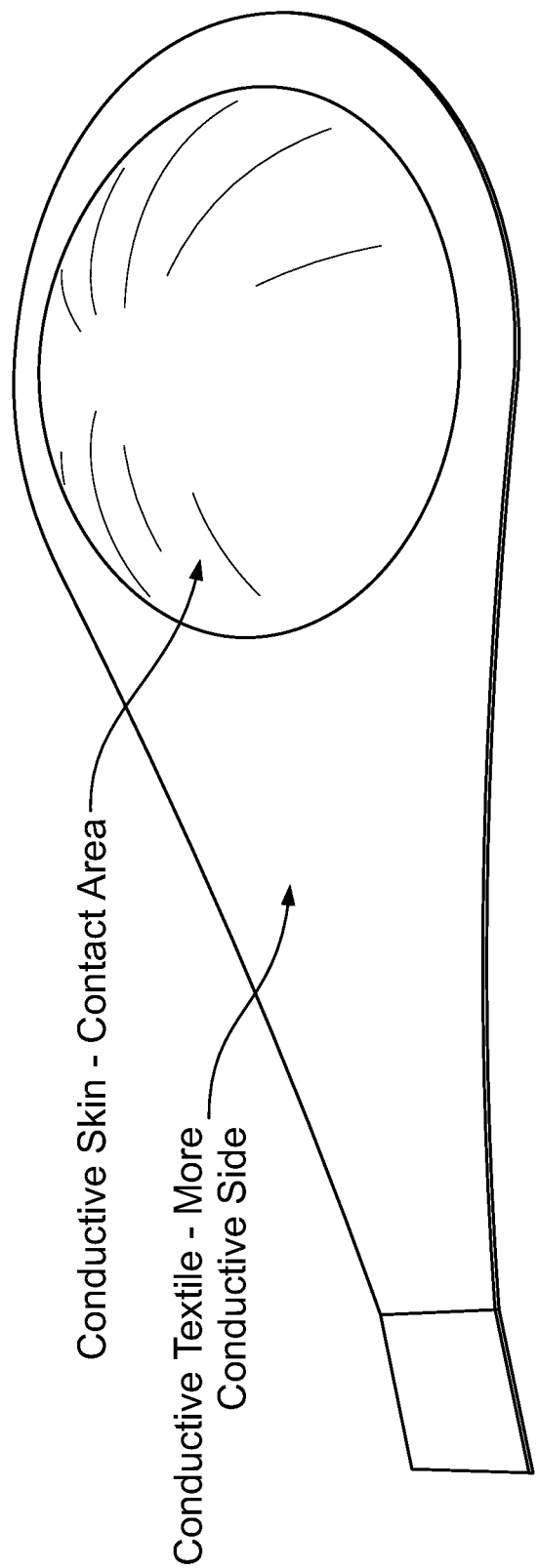
FIG. 2 shows an electrode according to some embodiments of the present invention.

FIG. 2 shows an electrode according to some embodiments of the present invention. In the embodiment shown, the electrode consists of a teardrop-shaped electrically conductive fabric, with a flat portion that terminates at one end with a connection to a printed circuit board, and a dome-shaped structure that forms a skin contact at the opposite end. In the embodiment shown, only the dome-shaped structure would be exposed and touch the skin of the pregnant human subject.

Figure 3:
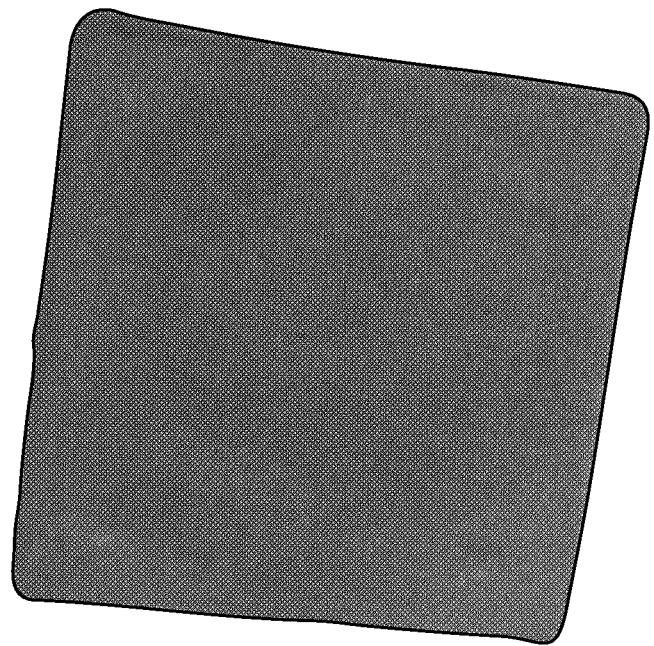
FIG. 3 shows an electrode according to some embodiments of the present invention.
Figure 4:
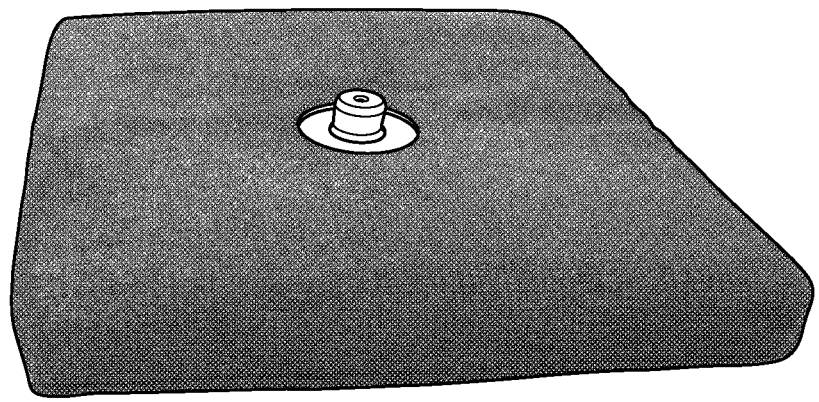
FIG. 4 shows an electrode according to some embodiments of the present invention.

FIGS. 3 and 4 show alternate embodiments of electrodes according to the present invention comprising a planar cutaneous contact.

In the embodiment shown in FIG. 1, the elastomeric dome shaped circular structure is configured to maximize contact between the cutaneous contact and the skin of the pregnant human subject under a all possible attachment angles.

In the embodiment shown in FIG. 1, the elastomeric dome shaped circular structure is configured to generate a profile without sharp angles which are likely to affect performance of the electrode.

In some embodiments, the elastomeric dome shaped circular structure has a diameter ranging from 20 to 50 mm. In some embodiments, the elastomeric dome shaped circular structure has a diameter of 20 mm. In some embodiments, the elastomeric dome shaped circular structure has a diameter of 25 mm. In some embodiments, the elastomeric dome shaped circular structure has a diameter of 30 mm. In some embodiments, the elastomeric dome shaped circular structure has a diameter of 35 mm. In some embodiments, the elastomeric dome shaped circular structure has a diameter of 40 mm. In some embodiments, the elastomeric dome shaped circular structure has a diameter of 45 mm. In some embodiments, the elastomeric dome shaped circular structure has a diameter of 50 mm.

In some embodiments, the elastomeric dome shaped circular structure has an un-deformed height (i.e. a height before pressure is applied) ranging from 5 to 15 mm. In some embodiments, the elastomeric dome shaped circular structure has an un-deformed height of 5 mm. In some embodiments, the elastomeric dome shaped circular structure has an un-deformed height of 10 mm. In some embodiments, the elastomeric dome shaped circular structure has an un-deformed height of 15 mm.

In some embodiments, the circular foam backing has a thickness ranging from 0.3 to 5 mm. In some embodiments, the circular foam backing has a thickness of 0.3 mm. In some embodiments, the circular foam backing has a thickness of 0.5 mm. In some embodiments, the circular foam backing has a thickness of 1 mm. In some embodiments, the circular foam backing has a thickness of 1.5 mm. In some embodiments, the circular foam backing has a thickness of 2 mm. In some embodiments, the circular foam backing has a thickness of 2.5 mm. In some embodiments, the circular foam backing has a thickness of 3 mm. In some embodiments, the circular foam backing has a thickness of 3.5 mm. In some embodiments, the circular foam backing has a thickness of 4 mm. In some embodiments, the circular foam backing has a thickness of 4.5 mm. In some embodiments, the circular foam backing has a thickness of 5 mm.

In the embodiment shown in FIG. 2, the elastomeric dome shaped circular structure is configured to generate a profile without sharp angles which are likely affect performance of the electrode. In some embodiments, the elastomeric dome shaped circular structure has a diameter ranging from 15 to 38 mm. In some embodiments, the elastomeric dome shaped circular structure has a diameter of 15 mm. In some embodiments, the elastomeric dome shaped circular structure has a diameter of 20 mm. In some embodiments, the elastomeric dome shaped circular structure has a diameter of 25 mm. In some embodiments, the elastomeric dome shaped circular structure has a diameter of 30 mm. In some embodiments, the elastomeric dome shaped circular structure has a diameter of 35 mm. In some embodiments, the elastomeric dome shaped circular structure has a diameter of 38 mm.

In some embodiments, the elastomeric dome shaped circular structure has an un-deformed height (i.e. a height before pressure is applied) ranging from 5 to 15 mm. In some embodiments, the elastomeric dome shaped circular structure has an un-deformed height of 5 mm. In some embodiments, the elastomeric dome shaped circular structure has an un-deformed height of 10 mm. In some embodiments, the elastomeric dome shaped circular structure has an un-deformed height of 15 mm.

Without intending to be limited to any particular theory, the skin-electrode impedance varies with the pressure at which the electrode contacts the skin of the pregnant human subject. In some embodiments, the skin-electrode impedance decreases as the pressure at which the electrode contacts the skin of the pregnant human subject increases.

In some embodiments, the elastomeric dome is configured to deform when placed on the abdomen of the pregnant human subject and pressure is applied to the electrode. In some embodiments, the elastomeric dome is configured to deform when placed on the abdomen of the pregnant human subject and pressure applied to create a skin-electrode impedance suitable for sensing fetal electrocardiogram signals from a pregnant human subject.

In some embodiments, the deformation of the elastomeric dome increases the surface area of the cutaneous contact that contacts the skin of the pregnant human subject. In some embodiments, 100% of the surface area of the cutaneous contact contacts the skin of the pregnant human subject. In an alternate embodiment, 90% of the surface area of the cutaneous contact contacts the skin of the pregnant human subject. In an alternate embodiment, 80% of the surface area of the cutaneous contact contacts the skin of the pregnant human subject. In an alternate embodiment, 70% of the surface area of the cutaneous contact contacts the skin of the pregnant human subject. In an alternate embodiment, 60% of the surface area of the cutaneous contact contacts the skin of the pregnant human subject. In an alternate embodiment, 50% of the surface area of the cutaneous contact contacts the skin of the pregnant human subject. In an alternate embodiment, 40% of the surface area of the cutaneous contact contacts the skin of the pregnant human subject. In an alternate embodiment, 30% of the surface area of the cutaneous contact contacts the skin of the pregnant human subject. In an alternate embodiment, 20% of the surface area of the cutaneous contact contacts the skin of the pregnant human subject. In an alternate embodiment, 10% of the surface area of the cutaneous contact contacts the skin of the pregnant human subject. In an alternate embodiment, 75% of the surface area of the cutaneous contact contacts the skin of the pregnant human subject.

In some embodiments, the pressure applied is equivalent to a mass ranging between 0.2 kg to 5 kg. In some embodiments, the pressure applied is equivalent to a mass of 0.2 kg. In some embodiments, the pressure applied is equivalent to a mass of 0.2 kg. In some embodiments, the pressure applied is equivalent to a mass of 0.3 kg. In some embodiments, the pressure applied is equivalent to a mass of 0.4 kg. In some embodiments, the pressure applied is equivalent to a mass of 0.5 kg. In some embodiments, the pressure applied is equivalent to a mass of 0.6 kg. In some embodiments, the pressure applied is equivalent to a mass of 0.7 kg. In some embodiments, the pressure applied is equivalent to a mass of 0.8 kg. In some embodiments, the pressure applied is equivalent to a mass of 0.9 kg. In some embodiments, the pressure applied is equivalent to a mass of 1 kg. In some embodiments, the pressure applied is equivalent to a mass of 1.5 kg. In some embodiments, the pressure applied is equivalent to a mass of 2 kg. In some embodiments, the pressure applied is equivalent to a mass of 2.5 kg. In some embodiments, the pressure applied is equivalent to a mass of 3 kg. In some embodiments, the pressure applied is equivalent to a mass of 3.5 kg. In some embodiments, the pressure applied is equivalent to a mass of 4 kg. In some embodiments, the pressure applied is equivalent to a mass of 4.5 kg. In some embodiments, the pressure applied is equivalent to a mass of 5 kg.

In some embodiments, the pressure is applied using a garment, such as a belt.

In some embodiments, the suitable skin-electrode impedance is between 100 and 650 k$\Omega$. In some embodiments, the suitable skin-electrode impedance is 602 k$\Omega$. In some embodiments, the suitable skin-electrode impedance is less than 150 k$\Omega$. In some embodiments, the suitable skin-electrode impedance is 227 k$\Omega$. In some embodiments, the suitable skin-electrode impedance is 135 k$\Omega$.

In some embodiments, the cutaneous contact is configured to have skin-electrode impedance of less than 150 k$\Omega$.

In some embodiments, the cutaneous contact is configured to have skin-electrode impedance of between 5 to 150 k$\Omega$. In some embodiments, the cutaneous contact is configured to have skin-electrode impedance of between 10 to 150 k$\Omega$. In some embodiments, the cutaneous contact is configured to have skin-electrode impedance of between 20 to 150 k$\Omega$. In some embodiments, the cutaneous contact is configured to have skin-electrode impedance of between 30 to 150 k$\Omega$. In some embodiments, the cutaneous contact is configured to have skin-electrode impedance of between 40 to 150 k$\Omega$. In some embodiments, the cutaneous contact is configured to have skin-electrode impedance of between 50 to 150 k$\Omega$. In some embodiments, the cutaneous contact is configured to have skin-electrode impedance of between 60 to 150 k$\Omega$. In some embodiments, the cutaneous contact is configured to have skin-electrode impedance of between 70 to 150 k$\Omega$. In some embodiments, the cutaneous contact is configured to have skin-electrode impedance of between 80 to 150 k$\Omega$. In some embodiments, the cutaneous contact is configured to have skin-electrode impedance of between 90 to 150 kΩ. In some embodiments, the cutaneous contact is configured to have skin-electrode impedance of between 100 to 150 kΩ. In some embodiments, the cutaneous contact is configured to have skin-electrode impedance of between 110 to 150 kΩ. In some embodiments, the cutaneous contact is configured to have skin-electrode impedance of between 120 to 150 kΩ. In some embodiments, the cutaneous contact is configured to have skin-electrode impedance of between 130 to 150 kΩ. In some embodiments, the cutaneous contact is configured to have skin-electrode impedance of between 140 to 150 kΩ.

In some embodiments, the cutaneous contact is attached to an elastomeric structure that is configured to deform when placed on the abdomen of the pregnant human subject to create a skin-electrode impedance of less than 150 kΩ.

In some embodiments, the cutaneous contact is attached to an elastomeric structure that is configured to deform when placed on the abdomen of the pregnant human subject to create a skin-electrode impedance of between 5 to 150 kΩ. In some embodiments, the cutaneous contact is attached to an elastomeric structure that is configured to deform when placed on the abdomen of the pregnant human subject to create a skin-electrode impedance of between 10 to 150 kΩ. In some embodiments, the cutaneous contact is attached to an elastomeric structure that is configured to deform when placed on the abdomen of the pregnant human subject to create a skin-electrode impedance of between 20 to 150 kΩ. In some embodiments, the cutaneous contact is attached to an elastomeric structure that is configured to deform when placed on the abdomen of the pregnant human subject to create a skin-electrode impedance of between 30 to 150 kΩ. In some embodiments, the cutaneous contact is attached to an elastomeric structure that is configured to deform when placed on the abdomen of the pregnant human subject to create a skin-electrode impedance of between 40 to 150 kΩ. In some embodiments, the cutaneous contact is attached to an elastomeric structure that is configured to deform when placed on the abdomen of the pregnant human subject to create a skin-electrode impedance of between 50 to 150 kΩ. In some embodiments, the cutaneous contact is attached to an elastomeric structure that is configured to deform when placed on the abdomen of the pregnant human subject to create a skin-electrode impedance of between 60 to 150 kΩ. In some embodiments, the cutaneous contact is attached to an elastomeric structure that is configured to deform when placed on the abdomen of the pregnant human subject to create a skin-electrode impedance of between 70 to 150 kΩ. In some embodiments, the cutaneous contact is attached to an elastomeric structure that is configured to deform when placed on the abdomen of the pregnant human subject to create a skin-electrode impedance of between 80 to 150 kΩ. In some embodiments, the cutaneous contact is attached to an elastomeric structure that is configured to deform when placed on the abdomen of the pregnant human subject to create a skin-electrode impedance of between 90 to 150 kΩ. In some embodiments, the cutaneous contact is attached to an elastomeric structure that is configured to deform when placed on the abdomen of the pregnant human subject to create a skin-electrode impedance of between 100 to 150 kΩ. In some embodiments, the cutaneous contact is attached to an elastomeric structure that is configured to deform when placed on the abdomen of the pregnant human subject to create a skin-electrode impedance of between 110 to 150 kΩ. In some embodiments, the cutaneous contact is attached to an elastomeric structure that is configured to deform when placed on the abdomen of the pregnant human subject to create a skin-electrode impedance of between 120 to 150 kΩ. In some embodiments, the cutaneous contact is attached to an elastomeric structure that is configured to deform when placed on the abdomen of the pregnant human subject to create a skin-electrode impedance of between 130 to 150 kΩ. In some embodiments, the cutaneous contact is attached to an elastomeric structure that is configured to deform when placed on the abdomen of the pregnant human subject to create a skin-electrode impedance of between 140 to 150 kΩ.

In some embodiments, the electrode is configured to have a surface resistance suitable for sensing fetal electrocardiogram signals from a pregnant human subject. In some embodiments, the cutaneous contact is configured to have a surface resistance of less than 1 Ω/square. In some embodiments, the cutaneous contact is configured to have a surface resistance between 0.01 and 1 Ω/square.

In some embodiments, the cutaneous contact is configured to have a surface resistance of 0.01 Ω/square. In some embodiments, the cutaneous contact is configured to have a surface resistance of 0.02 Ω/square. In some embodiments, the cutaneous contact is configured to have a surface resistance of 0.03 Ω/square. In some embodiments, the cutaneous contact is configured to have a surface resistance of 0.04 Ω/square. In some embodiments, the cutaneous contact is configured to have a surface resistance of 0.05 Ω/square. In some embodiments, the cutaneous contact is configured to have a surface resistance of 0.06 Ω/square. In some embodiments, the cutaneous contact is configured to have a surface resistance of 0.07 Ω/square. In some embodiments, the cutaneous contact is configured to have a surface resistance of 0.08 Ω/square. In some embodiments, the cutaneous contact is configured to have a surface resistance of 0.09 Ω/square. In some embodiments, the cutaneous contact is configured to have a surface resistance of 0.1 Ω/square. In some embodiments, the cutaneous contact is configured to have a surface resistance of 0.2 Ω/square. In some embodiments, the cutaneous contact is configured to have a surface resistance of 0.3 Ω/square. In some embodiments, the cutaneous contact is configured to have a surface resistance of 0.4 Ω/square. In some embodiments, the cutaneous contact is configured to have a surface resistance of 0.5 Ω/square. In some embodiments, the cutaneous contact is configured to have a surface resistance of 0.6 Ω/square. In some embodiments, the cutaneous contact is configured to have a surface resistance of 0.7 Ω/square. In some embodiments, the cutaneous contact is configured to have a surface resistance of 0.8 Ω/square. In some embodiments, the cutaneous contact is configured to have a surface resistance of 0.9 Ω/square. In some embodiments, the cutaneous contact is configured to have a surface resistance of 1 Ω/square.

In some embodiments, the electrode is configured to have a capacitance suitable for sensing fetal electrocardiogram signals from a pregnant human subject. In some embodiments, the capacitance is from 1 nF to 0.5 μF. In some embodiments, the capacitance is 5 nF. In some embodiments, the capacitance is 10 nF. In some embodiments, the capacitance is 15 nF. In some embodiments, the capacitance is 20 nF. In some embodiments, the capacitance is 25 nF. In some embodiments, the capacitance is 30 nF. In some embodiments, the capacitance is 35 nF. In some embodiments, the capacitance is 40 nF. In some embodiments, the capacitance is 45 nF. In some embodiments, the capacitance is 50 nF. In some embodiments, the capacitance is 60 nF. In some embodiments, the capacitance is 70 nF. In some embodiments, the capacitance is 80 nF. In some embodiments, the capacitance is 90 nF. In some embodiments, the capacitance is 80 nF. In some embodiments, the capacitance is 0.1 µF. In some embodiments, the capacitance is 80 nF. In some embodiments, the capacitance is 0.2 µF. In some embodiments, the capacitance is 80 nF. In some embodiments, the capacitance is 0.3 µF. In some embodiments, the capacitance is 80 nF. In some embodiments, the capacitance is 0.4 µF. In some embodiments, the capacitance is 80 nF. In some embodiments, the capacitance is 0.5 µF.

Without intending to be limited to any particular theory, the capacitance of the electrodes increases as the surface area of the cutaneous contact that contacts the skin of the pregnant human subject increases. Additionally, without intending to be limited to any particular theory, the capacitance of the electrodes decreases as the pressure applied to the cutaneous contact increases.

In some embodiments, the electrode is configured to detect a fetal electrocardiogram signal having a signal to noise ratio between −20 dB and 50 dB. In some embodiments, the electrode is configured to detect a fetal electrocardiogram signal having a signal to noise ratio between 0 dB and 50 dB. In some embodiments, the electrode is configured to detect a fetal electrocardiogram signal having a signal to noise ratio less than 50 dB.

The Cutaneous Contact

In some embodiments, the cutaneous contact is an electrically conductive fabric. Electrically conductive fabrics can be made with conductive fibers, such as, for example, metal strands woven into the construction of the fabric. Examples of electrically conductive fabrics suitable for use in electrodes according to some embodiments of the present invention include, but are not limited to, the textile electrodes disclosed in *Sensors*, 12 16907-16919, 2012. Another example of electrically conductive fabrics suitable for use in electrodes according to some embodiments of the present invention include, but are not limited to, the textile electrodes disclosed in *Sensors*, 14 11957-11992, 2014.

The electrically conductive fabric may be stretchable. Alternatively, the electrically conductive fabric may not be stretchable. The electrically conductive fabric may be capable of stretching up to 50%, alternatively, 40%, alternatively, 30%, alternatively 20%, alternatively 20%, alternatively, 10%, alternatively, 9%, alternatively, 8%, alternatively, 7%, alternatively, 6%, alternatively, 5%, alternatively, 4%, alternatively, 3%, alternatively, 2%, alternatively, 1%.

In some embodiments, the electrically conductive fabric is anisotropic. In some embodiments, the anisotropy is from 50% to 100%. As used herein, the term anisotropy refers to the difference in resistance of the electrically conductive fabric measured in the main direction, compared to the direction perpendicular to the main direction. As used herein, the term "main direction refers to the direction that the fabric was woven. In some embodiments, the anisotropy of the electrically conductive fabric is configured to have an anisotropy suitable for sensing fetal electrocardiogram signals from a pregnant human subject. In some embodiments, the anisotropy is 62%.

In some embodiments, the electrically conductive fabric is configured to be oriented so the current recorded is the electrical activity that is generated by the fetal and/or maternal heart, and flows along the main direction of the fabric to the lead wire. In some embodiments, the electrically conductive fabric is configured to be oriented so the current recorded is the electrical activity that is generated by the fetal and/or maternal heart, and flows along the direction of the fabric having the least resistance to the lead wire.

In some embodiments, the conductivity of one side of the electrically conductive fabric is greater than the other. In some embodiments, the side of the electrically conductive fabric with the greater conductivity forms cutaneous contact.

In some embodiments, the electrically conductive fabric has a thickness between 0.3 and 0.5 mm. In some embodiments, the thickness of the electrically conductive fabric is 0.3 mm. In some embodiments, the thickness of the electrically conductive fabric is 0.4 mm. In some embodiments, the thickness of the electrically conductive fabric is 0.5 mm.

Figure 5:
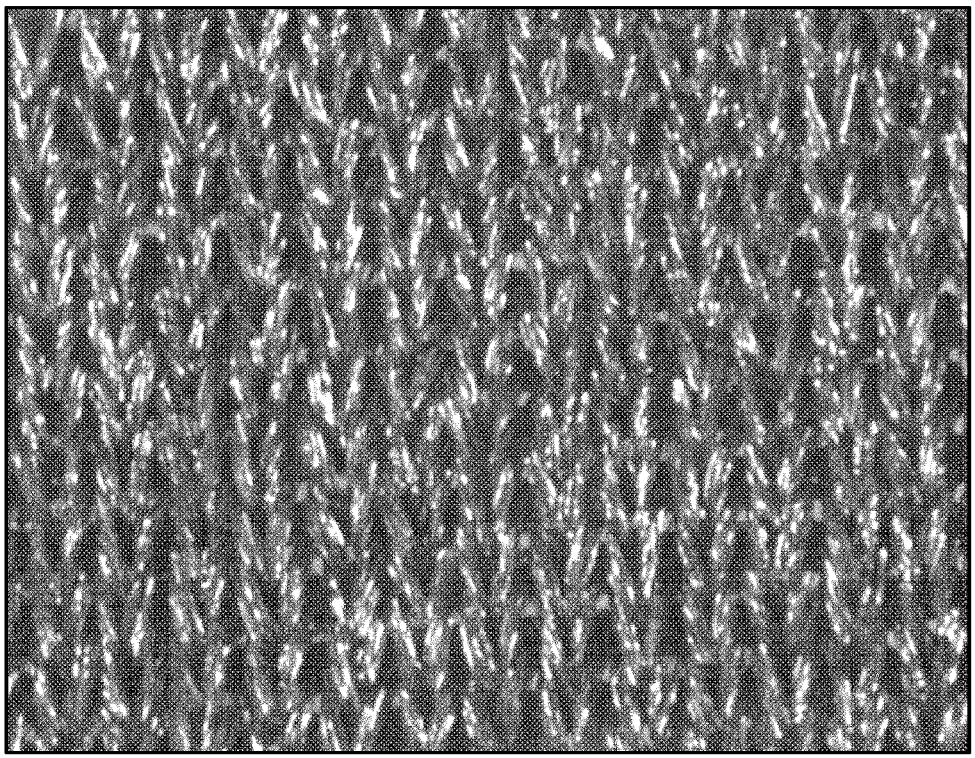
FIG. 5 shows a micrograph of electrically conductive fabric suitable as a cutaneous contact according to some embodiments of the present invention.

In some embodiments, the electrically conductive fabric is the silver-based conductive fabric sold under the tradename ORANGE IT. An example of this electrically conductive fabric is shown in FIG. 5.

Figure 6:
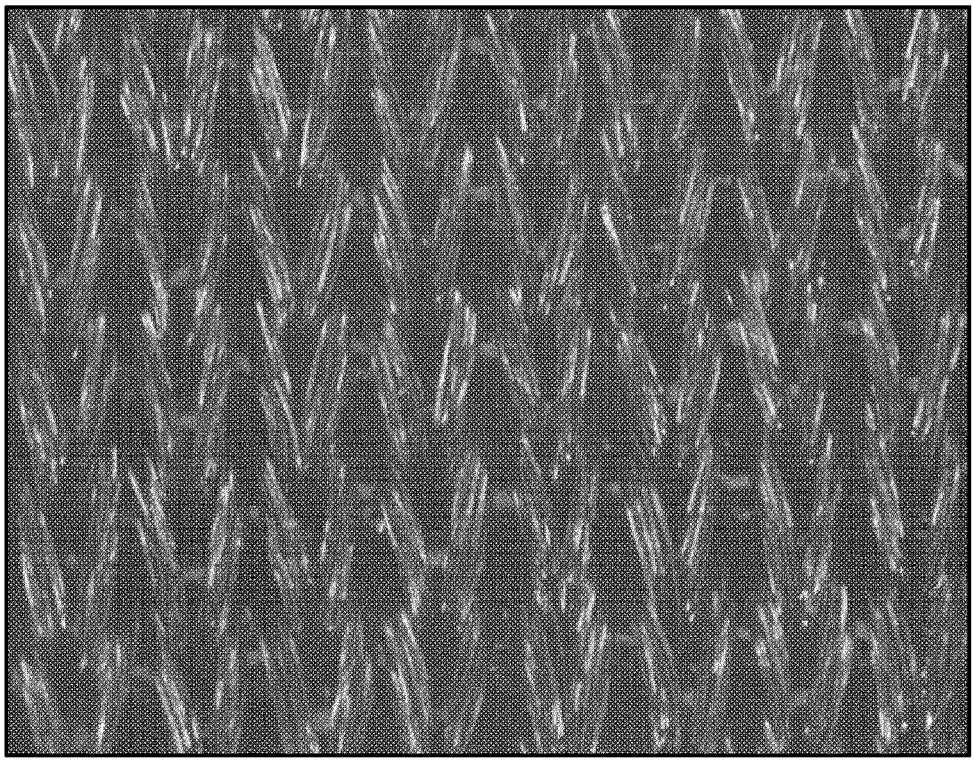
FIG. 6 shows a micrograph of electrically conductive fabric suitable as a cutaneous contact according to some embodiments of the present invention.

In some embodiments, the electrically conductive fabric is the silver-based conductive fabric sold under the tradename C+, sold by Clothing+, St. Petersburg, Fla., USA. An example of this electrically conductive fabric is shown in FIG. 6.

Figure 7:
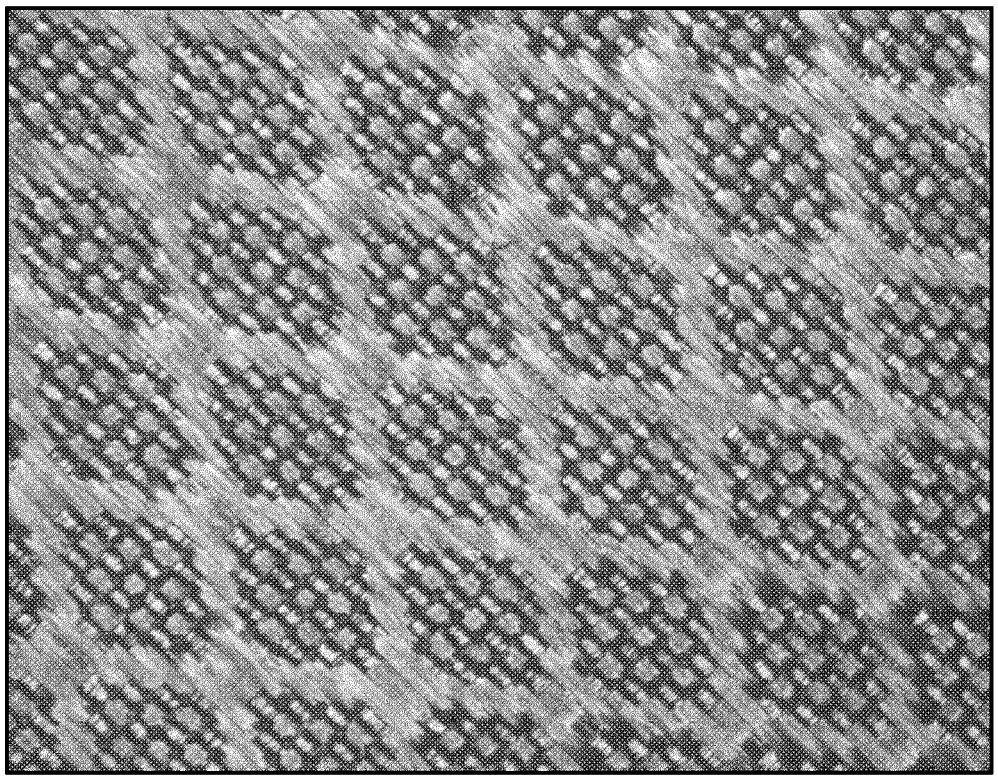
FIG. 7 shows a micrograph of electrically conductive fabric suitable as a cutaneous contact according to some embodiments of the present invention.

In some embodiments, the electrically conductive fabric is the silver-based conductive fabric sold under the tradename SHAOXING17, sold by Shaoxing Yunjia Textile Prodict Co. Ltd., Zhejiang, China. An example of this electrically conductive fabric is shown in FIG. 7.

Figure 8:
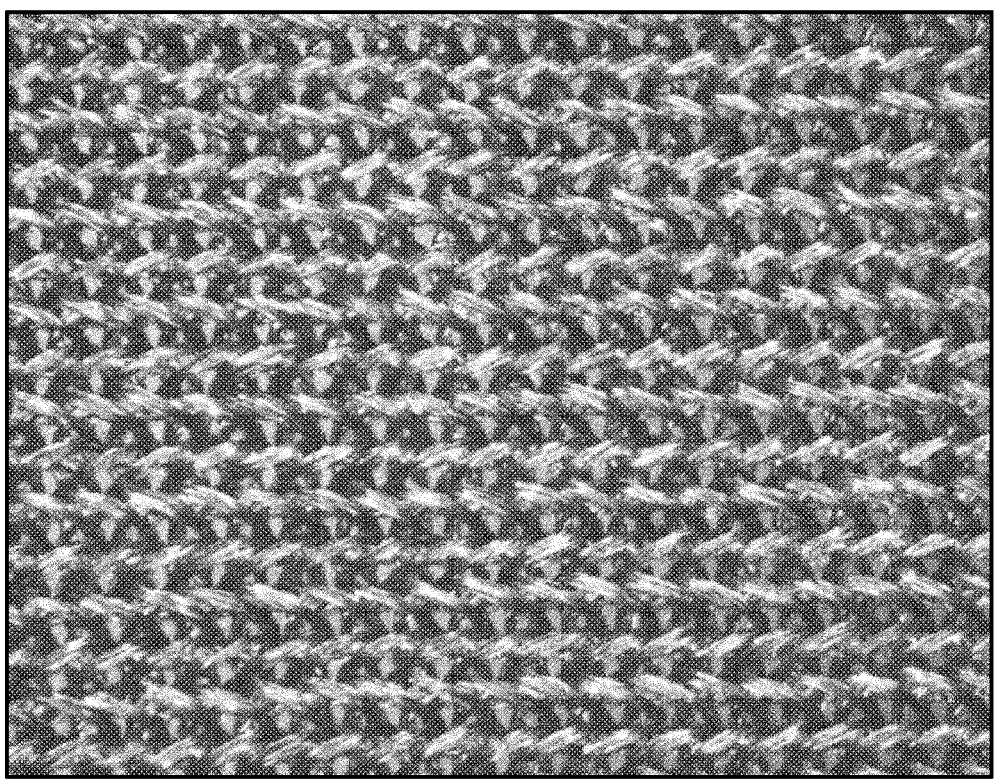
FIG. 8 shows a micrograph of electrically conductive fabric suitable as a cutaneous contact according to some embodiments of the present invention.

In some embodiments, the electrically conductive fabric is the silver-based conductive fabric sold under the tradename SHAOXING27, sold by Shaoxing Yunjia Textile Prodict Co. Ltd., Zhejiang, China. An example of this electrically conductive fabric is shown in FIG. 8.

Figure 9:
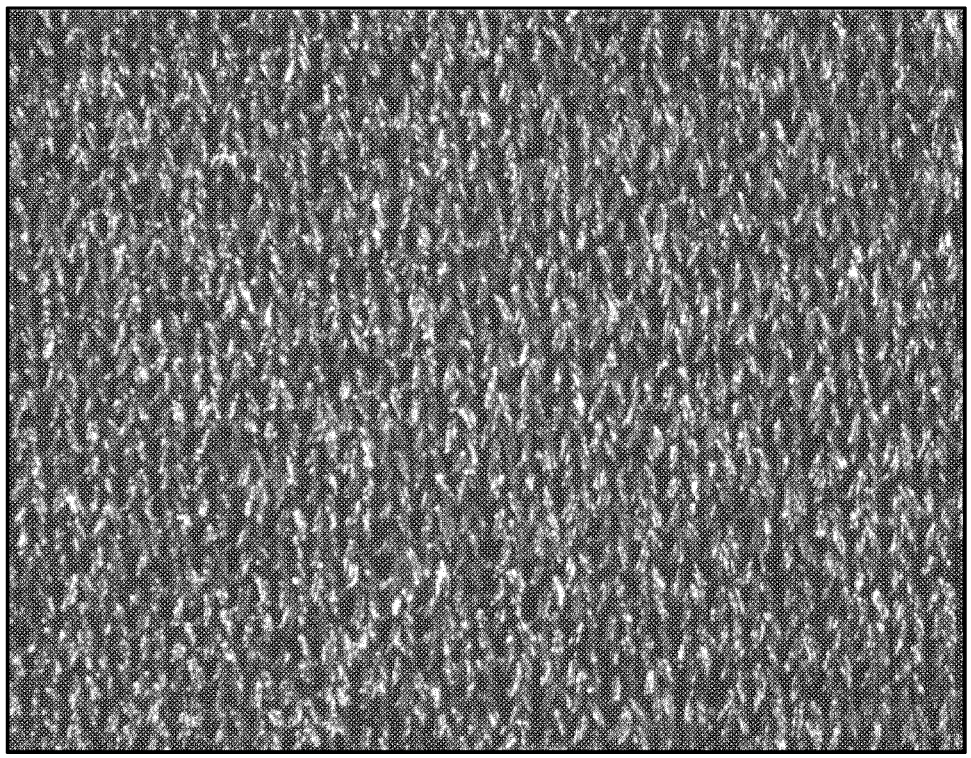
FIG. 9 shows a micrograph of electrically conductive fabric suitable as a cutaneous contact according to some embodiments of the present invention.

In some embodiments, the electrically conductive fabric is the silver-based conductive fabric sold under the tradename SHIELDEX TECHNIK-TEX P130-B, sold by Shieldex Trading USA, Palmyra, N.Y., USA. An example of this electrically conductive fabric is shown in FIG. 9.

Figure 10:
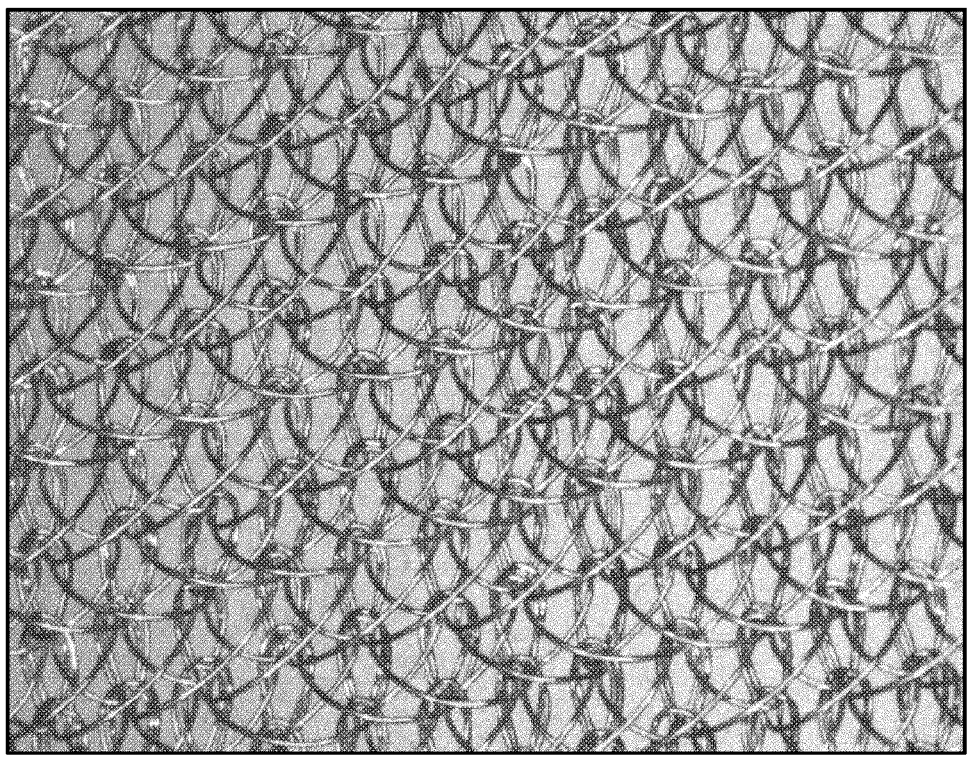
FIG. 10 shows a micrograph of electrically conductive fabric suitable as a cutaneous contact according to some embodiments of the present invention.

In some embodiments, the electrically conductive fabric is the silver-based conductive fabric sold under the tradename SILVER30, sold by Shaoxing Yunjia Textile Prodict Co. Ltd., Zhejiang, China. An example of this electrically conductive fabric is shown in FIG. 10.

Systems for Sensing Fetal Cardiac Electrical Activity

In some embodiments, the arrangement of the electrodes provides a system for recording, detecting and analyzing fetal cardiac electrical activity data regardless of sensor position, fetal orientation, fetal movement, or gestational age. In some embodiments, the electrodes are attached, or positioned, on the abdomen of the pregnant human subject in the configuration shown in FIG. 11. In some embodiments, the electrodes are divided into channels comprising a pair of electrodes, and cardiac electrical activity data is recorded simultaneously from the channels. In some embodiments, the channels output the acquired signal data, corresponding to the recorded cardiac electrical activity data.

Figure 12:
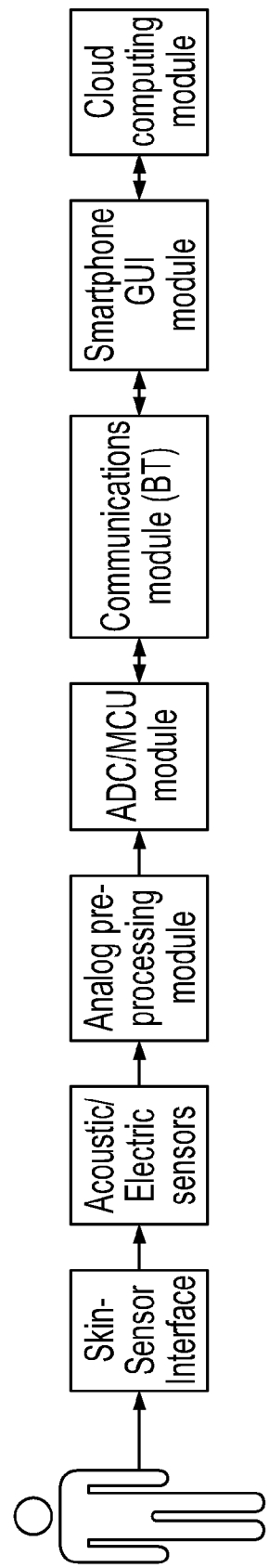
FIG. 12 shows a representation of a system suitable for use in fetal heart rate monitoring systems according to some embodiments of the present invention.

Referring to FIG. 12, in some embodiments, the system for recording, detecting and analyzing fetal cardiac electrical activity comprises a skin-electrode interface, at least one electrode, an analog pre-processing module, an analog to digital converter/microcontroller (ADC/MCU) module, a communications module, a smartphone module, and a cloud computing module.

In some embodiments, the analog pre-processing module performs at least one function selected from the group consisting of: amplification of the recorded signals, and filtering the recorded signals.

In some embodiments, the ADC/MCU module performs at least one task selected from the group consisting of: converting analog signals to digital signals, converting the recorded signals to digital signals, compressing the data, digital filtering, and transferring the recorded electrocardiogram signals data to the transmitter.

In some embodiments, the communications module transmits the recorded signals to a wireless receiver.

In some embodiments, the system for recording, detecting and analyzing fetal cardiac electrical activity data regardless of sensor position, fetal orientation, fetal movement, or gestational age is the system disclosed in International Patent Application Serial No. PCT/IL2015/050407.

In some embodiments, at least one electrode pair is used to obtain the acquired signal data. In some embodiments, For example, by way of a non-limiting illustration, in some embodiments, the channels are specified as follows:
1. B1-B3
2. B1-B2
3. B2-B3
4. A1-A4
5. A2-A3
6. A2-A4

In some embodiments, the signal data corresponding to fetal cardiac electrical activity data are extracted from the acquired signal data.

In some embodiments, the signal data corresponding to fetal cardiac electrical activity data are extracted from the acquired signal data according to the methods described in U.S. patent application Ser. No. 14/921,489.

In one embodiment, the present invention provides a garment, comprising:

at least one pair of electrodes,
wherein the at least one pair of electrodes are configured, when the garment is worn by the pregnant human subject, such that the individual electrodes of the at least one electrode pair encircle the uterus of the pregnant human subject, and
wherein the individual electrodes of the at least one electrode pair comprise:
a) a cutaneous contact for sensing fetal electrocardiogram signals from a pregnant human subject;
b) a connector in electrical contact with the cutaneous contact for connection to a lead wire; and
c) a substructure for attachment to a human pregnant subject
wherein, the cutaneous contact is configured on the substructure to allow a surface of the cutaneous contact to be in electrical communication with the skin of the pregnant human subject;
wherein cardiac electrical activity data is recorded from the at least one sensor pair.

Figure 13:
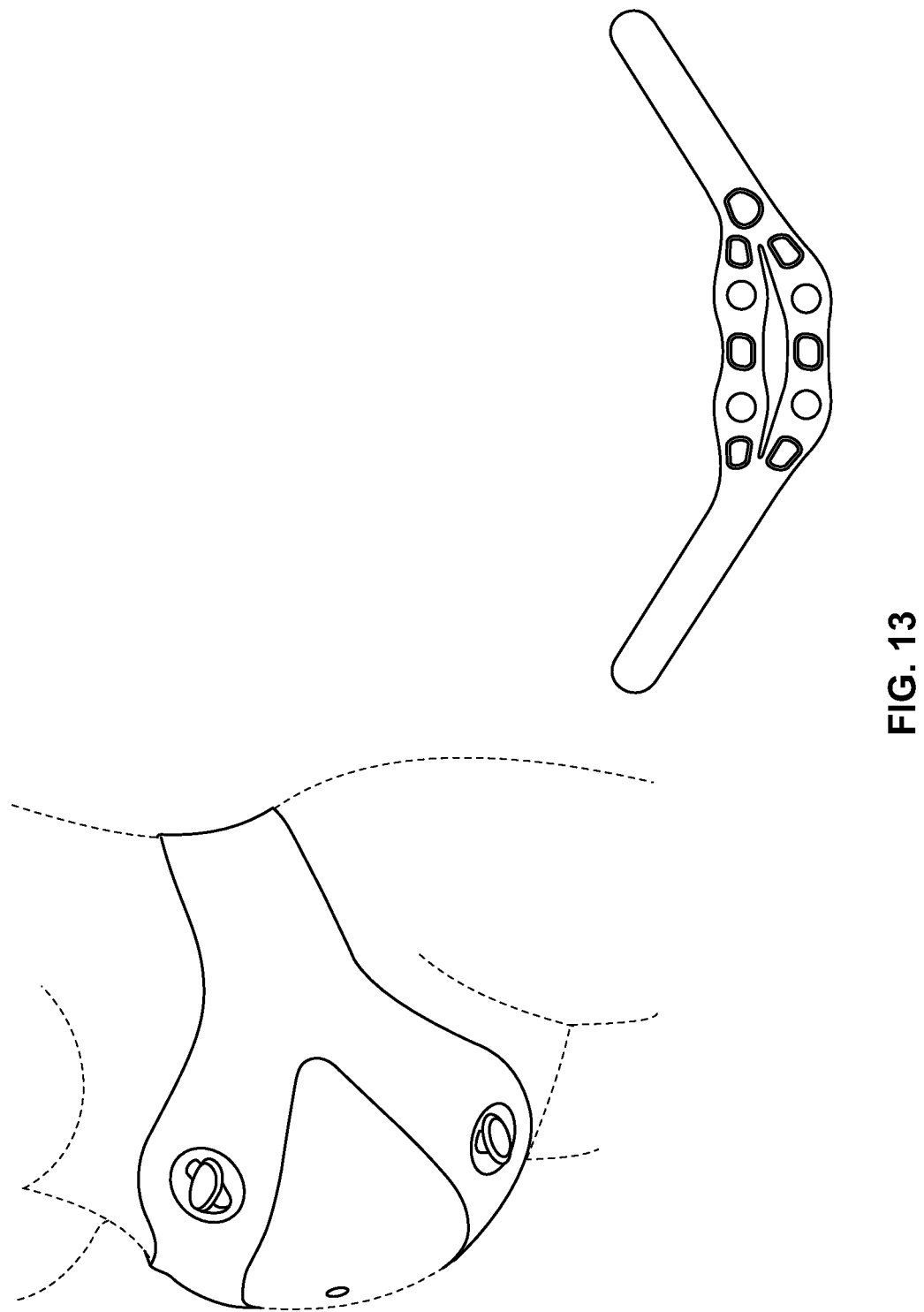
FIG. 13 shows a garment according to some embodiments of the present invention.

Referring to FIG. 13, an example of a garment according to some embodiments of the present invention is shown. In the embodiment shown, 6 electrodes are incorporated into a belt, wherein the belt, when worn, positions the electrodes on the abdomen of the pregnant mother, such that the electrodes contact the skin of the abdomen of the pregnant mother, and the electrodes are positioned in a circumferential arrangement around the uterus. In the embodiments shown, the belt also contains additional sensors and a transmitter.

In some embodiments, the additional sensors are acoustic sensors.

Reference is now made to the following examples, which together with the above descriptions illustrate some embodiments of the invention in a non-limiting fashion.

EXAMPLES

Example 1

Electrodes According to Some Embodiments of the Present Invention

Various electrodes were manufactured according to the embodiment shown in FIG. 1 and evaluated. The following parameters were tested: the surface resistance/resistivity (MSSR); basic transfer function testing (BTFT); bio-parameters (PhysioPM); and real-life recordings of fetal cardiac electrical signals (RLPysioPM). Table 1 summarizes the electrodes tested.

TABLE 1

| Serial# | ID | Surface conductivity [Ohm/Sq] | Measured* Surface conductivity [Ohm/Sq] | Available size [cm × cm] | Materials | Notes |
|---|---|---|---|---|---|---|
| 1 | Orange_IT | <2 | 3.5 | 20*20 | Silver | Anisotropic, Stechable |
| 2 | C+ | <4 | 4 | 70*70 | Silver | Anisotropic, Stechable |
| 3 | Shaoxing17 | — | 0.3 | 1 m^2 | Silver | Isotropic, Non-strechable |
| 4 | Shaoxing27 | — | 0.6 | 1 m^2 | Silver | Isotropic, Non-strechable |
| 5 | Tech P130 + B | <5 | 1.1 | 40*40 | Silver | Isotropic, Strechable |
| 6 | Silver30 | — | 3.5 | 20*15 | Silver | Isotropic, Strechable |

FIG. 5 shows a micrograph of electrically conductive fabric used electrode serial no. 1. FIG. 6 shows a micrograph of electrically conductive fabric used electrode serial no. 2. FIG. 7 shows a micrograph of electrically conductive fabric used electrode serial no. 3. FIG. 8 shows a micrograph of electrically conductive fabric used electrode serial no. 4. FIG. 9 shows a micrograph of electrically conductive fabric used electrode serial no. 5. FIG. 10 shows a micrograph of electrically conductive fabric used electrode serial no. 6.

Table 2 a-f shows the MSSR values observed from the electrodes tested. Table 3 shows the observed anisotropy of the electrodes tested.

TABLE 2a

| | | Sens 1 | | | | | | |
|---|---|---|---|---|---|---|---|---|
| Inject | Measure | Check? | M1 | M2 | M3 | AVG [Ω] | Anisotropic | Notes |
| AB | CD | 1 | 0.243 | 0.245 | 0.246 | 0.245 | 0.230 | |
| CD | AB | 1 | 0.228 | 0.227 | 0.226 | 0.227 | | |
| BA | DC | 1 | 0.224 | 0.225 | 0.222 | 0.224 | | |
| DC | BA | 1 | 0.227 | 0.224 | 0.222 | 0.224 | | |
| BC | DA | 1 | 0.489 | 0.487 | 0.484 | 0.487 | 0.459 | |
| DA | BC | 0 | 0 | 0 | 0 | 0.000 | | |

TABLE 2a-continued

Sens 1

| Inject | Measure | Check? | M1 | M2 | M3 | AVG [Ω] | Anisotropic | Notes |
|---|---|---|---|---|---|---|---|---|
| CB | DA | 1 | 0.444 | 0.443 | 0.441 | 0.443 | | |
| AD | CB | 1 | 0.45 | 0.448 | 0.446 | 0.448 | | |

TABLE 2b

Sens 2

| Inject | Measure | Check? | M1 | M2 | M3 | AVG [Ω] | Anisotropic | Notes |
|---|---|---|---|---|---|---|---|---|
| AB | CD | 1 | 1.022 | 1.02 | 1.014 | 1.019 | 1.032 | |
| CD | AB | 1 | 0.999 | 0.996 | 0.995 | 0.997 | | |
| BA | DC | 1 | 0.994 | 0.984 | 0.979 | 0.986 | | |
| DC | BA | 1 | 1.13 | 1.123 | 1.123 | 1.125 | | |
| BC | DA | 0 | 0 | 0 | 0 | 0.000 | NaN | Main direction |
| DA | BC | 0 | 0 | 0 | 0 | 0.000 | | |
| CB | AD | 0 | 0 | 0 | 0 | 0.000 | | |
| AD | CB | 0 | 0 | 0 | 0 | 0.000 | | |

TABLE 2c

Sens 3

| Inject | Measure | Check? | M1 | M2 | M3 | AVG [Ω] | Isotropic | Notes |
|---|---|---|---|---|---|---|---|---|
| AB | CD | 1 | 0.039 | 0.038 | 0.04 | 0.039 | 0.031 | |
| CD | AB | 1 | 0.027 | 0.024 | 0.025 | 0.025 | | |
| BA | DC | 1 | 0.023 | 0.023 | 0.023 | 0.023 | | |
| DC | BA | 1 | 0.036 | 0.035 | 0.035 | 0.035 | | |
| BC | DA | 1 | 0.026 | 0.028 | 0.026 | 0.027 | 0.026 | |
| DA | BC | 1 | 0.024 | 0.025 | 0.023 | 0.024 | | |
| CB | AD | 1 | 0.027 | 0.026 | 0.026 | 0.026 | | |
| AD | CB | 1 | 0.027 | 0.024 | 0.026 | 0.026 | | |

TABLE 2d

Sens 4

| Inject | Measure | Check? | M1 | M2 | M3 | AVG [Ω] | Isotropic | Notes |
|---|---|---|---|---|---|---|---|---|
| AB | CD | 1 | 0.026 | 0.063 | 0.064 | 0.051 | 0.058 | |
| CD | AB | 1 | 0.058 | 0.057 | 0.059 | 0.058 | | |
| BA | DC | 1 | 0.06 | 0.059 | 0.058 | 0.059 | | |
| DC | BA | 1 | 0.066 | 0.065 | 0.066 | 0.066 | | |
| BC | DA | 1 | 0.045 | 0.045 | 0.045 | 0.045 | 0.044 | |
| DA | BC | 1 | 0.043 | 0.044 | 0.043 | 0.043 | | |
| CB | AD | 1 | 0.045 | 0.043 | 0.043 | 0.044 | | |
| AD | CB | 1 | 0.044 | 0.042 | 0.043 | 0.043 | | |

TABLE 2e

Sens 5

| Inject | Measure | Check? | M1 | M2 | M3 | AVG [Ω] | Anisotropic | Notes |
|---|---|---|---|---|---|---|---|---|
| AB | CD | 1 | 0.222 | 0.224 | 0.223 | 0.223 | 0.194 | |
| CD | AB | 1 | 0.212 | 0.211 | 0.213 | 0.212 | | |
| BA | DC | 1 | 0.22 | 0.219 | 0.222 | 0.220 | | |
| DC | BA | 1 | 0.233 | 0.065 | 0.066 | 0.121 | | |
| BC | DA | 1 | 0.074 | 0.073 | 0.073 | 0.073 | 0.075 | |
| DA | BC | 1 | 0.083 | 0.084 | 0.084 | 0.084 | | |
| CB | AD | 1 | 0.074 | 0.075 | 0.075 | 0.075 | | |
| AD | CB | 1 | 0.065 | 0.067 | 0.067 | 0.066 | | |

TABLE 2f

Sens 6

| Inject | Measure | Check? | M1 | M2 | M3 | AVG [Ω] | Anisotropic | Notes |
|---|---|---|---|---|---|---|---|---|
| AB | CD | 1 | 0.05 | 0.048 | 0.049 | 0.049 | 0.046 | |
| CD | AB | 1 | 0.038 | 0.039 | 0.037 | 0.038 | | |
| BA | DC | 1 | 0.055 | 0.057 | 0.056 | 0.056 | | |
| DC | BA | 1 | 0.043 | 0.041 | 0.042 | 0.042 | | |
| BC | DA | 1 | 0.911 | 0.903 | 0.898 | 0.904 | 0.898 | |
| DA | BC | 1 | 0.904 | 0.891 | 0.897 | 0.897 | | |
| CB | AD | 1 | 0.885 | 0.886 | 0.882 | 0.884 | | |
| AD | CB | 1 | 0.903 | 0.903 | 0.908 | 0.905 | | |

TABLE 3

| ID | Main direction | 2nd direction | Anisotropy |
|---|---|---|---|
| 1 | 0.230 | 0.459 | 50% |
| 2 | 0.000* | 1.032 | 100% |
| 3 | 0.026 | 0.031 | 16% |
| 4 | 0.044 | 0.058 | 25% |
| 5 | 0.075 | 0.194 | 62% |
| 6 | 0.046 | 0.898 | 95% |

The impedance between the fabric and the lead connector was also determined. The electrodes were connected to a copper sheet, and a pressure of 34.386 kPa was applied, using a 1.01026 kg weight. The measured impedance of the measuring system was 0.109 Ω, and this value was subtracted from the measured impedance of the electrodes. The results are shown in Table 4. Electrode serial no. 5 was observed to have the greatest surface area in contact with the surface.

TABLE 4

| ID | Check? | M1 | M2 | M3 | AVG [Ω] | Value [Ω] |
|---|---|---|---|---|---|---|
| 1 | 1 | 0.694 | 0.685 | 0.682 | 0.687 | 0.578 |
| 2 | 1 | 0.461 | 0.460 | 0.452 | 0.458 | 0.349 |
| 3 | 1 | 0.206 | 0.205 | 0.206 | 0.206 | 0.097 |
| 4 | 1 | 0.271 | 0.269 | 0.268 | 0.269 | 0.160 |
| 5 | 1 | 0.309 | 0.307 | 0.308 | 0.308 | 0.199 |
| 6 | 1 | 0.709 | 0.662 | 0.664 | 0.678 | 0.569 |

Electrodes 3-5 performed best. Performance was scored as follows:

| Req. ID | Test Category | Category | Details |
|---|---|---|---|
| 0.1 | Performance | General | Record ECG signals |
| 1.1 | Performance | MSRR | Surface resistivity below 1 [Ω · m] |
| 1.2 | Performance | MSRR | Surface resistance below 1 [Ω/sq] |
| 2.1 | Performance | BTFT | SINAD is higher than 50 dB |
| 2.2 | Performance | BTFT | SNR is higher than 50 dB |
| 2.3 | Performance | BTFT | CORR COEF higher than 0.95 |

-continued

| Req. ID Category | Test Category | Details |
|---|---|---|
| 3.1 Performance | PysioPM | Skin-Sensor impedance below 0.15 [MΩ] |
| 3.2 Performance | PysioPM | Self-noise of the sensor below 0.1 μV |
| 3.3 Performance | PysioPM | Immunity to motion artifacts |
| 3.4 Performance | PysioPM | Power-line noise rejection higher than 80 dB |
| 4.1 Performance | RLPysioPM | Fetal ECG is visible in more than 1 record |
| 4.2 Performance | RLPysioPM | Fetal ECG SNR is higher than 1 dB |
| 3.5 Performance | RLPysioPM | Relative fetal ECG SNR (relative to the reference sensor) is higher than 0.85 |

A summary of the MSSR results for electrodes 3-5 is shown in Table 5. The fabric of electrode serial no. 6 was weak, and has large voids between the fibers (see FIG. 10) and was therefore unsuitable. Electrode serial no. 2 was excluded because the surface resistivity was greater than 1 Ω/square.

TABLE 5

| | Surface resistance | | | | |
|---|---|---|---|---|---|
| ID | Main direction | 2nd direction | Aniso-tropy | S2C | Notes |
| 3 | 0.026 | 0.031 | 0.163 | 0.097 | Lowest resistance, non-stretchable, Isotropic |
| 4 | 0.044 | 0.058 | 0.251 | 0.160 | Mid |
| 5 | 0.075 | 0.194 | 0.616 | 0.199 | Low resistance, Highest Anisotropy, highly stretchable |

BTFT Results: BTFT measurements were obtained using the methods described in Example 3 below. Table 6 shows the results.

TABLE 6

| | | | Relative diff RMS | SINAD | | | | SNR | | |
|---|---|---|---|---|---|---|---|---|---|---|
| ID | CORRCOEF | CORRLAG | [%] | Input | Output | Rel | RelRef | Input | Output | Rel |
| Ref | 1 | 0 | 0.012 | 48.545 | 48.541 | 0.008% | 0.000% | 53.852 | 53.836 | 0.029% |
| 1 | 1 | 0 | 0.010 | 47.964 | 47.956 | 0.015% | 1.205% | 54.278 | 54.242 | 0.066% |
| 2 | 1 | 0 | 0.016 | 48.088 | 48.077 | 0.021% | 0.955% | 54.173 | 54.136 | 0.068% |
| 3 | 1 | 0 | 0.010 | 48.231 | 48.222 | 0.018% | 0.657% | 54.197 | 54.161 | 0.067% |
| 4 | 1 | 0 | 0.015 | 48.303 | 48.293 | 0.020% | 0.511% | 54.042 | 54.006 | 0.066% |
| 5 | 1 | 0 | 0.015 | 48.527 | 48.517 | 0.020% | 0.049% | 54.137 | 54.102 | 0.064% |
| 6 | 1 | 0 | 0.014 | 48.606 | 48.597 | 0.018% | 0.115% | 54.113 | 54.073 | 0.074% |

CORRCOEF: is the linear correlation coefficient between the input and the output signals; CORRLAG: is the lag between the input and output signals; Relative diff RMS: is the relative difference in the RMS of the input and output signals in %; SINAD.Rel: is the relative percentage difference in the SINAD values between the input and the output signals; SINAD.RelRef: is the relative percentage difference in the signal to noise and distortion ratio (SINAD) values between the output signal and the reference signal; SNR.Rel: is the relative percentage difference in the SNR values between the input and the output signals. The BTFT results show that the electrodes that have the best performance in terms of SNR and relative SINAD is electrode serial no. 5 followed by electrode serial no. 4, then electrode serial no. 3.

PysioPM: PysioPM measurements were obtained according to the methods described in Example 4. Table 7 shows the results of the measured impedance.

TABLE 7

| ID | Sens1 | Sens2 | Sens3 | Sens4 | MAXDIFF |
|---|---|---|---|---|---|
| 3 | 0.733 | 0.667 | 0.651 | 0.754 | 13.66% |
| 4 | 1.396 | 1.495 | 1.281 | 1.503 | 14.77% |
| 5 | 4.251 | 3.1 | 3.551 | 3.921 | 27.08% |

The values observed include the resistance of a 5 cm lead wire, the copper sheet, and a cable connected to the copper sheet.

Impedance of the interface between the electrode and the skin: The impedance was measured between 2 electrodes placed on skin 20 mm apart. Table 8 shows the average of 3 experiments.

TABLE 8

| ID | Average Bioimpedance [MΩ] |
|---|---|
| 3 | 0.602 |
| 4 | 0.227 |
| 5 | 0.135 |

Figure 14:
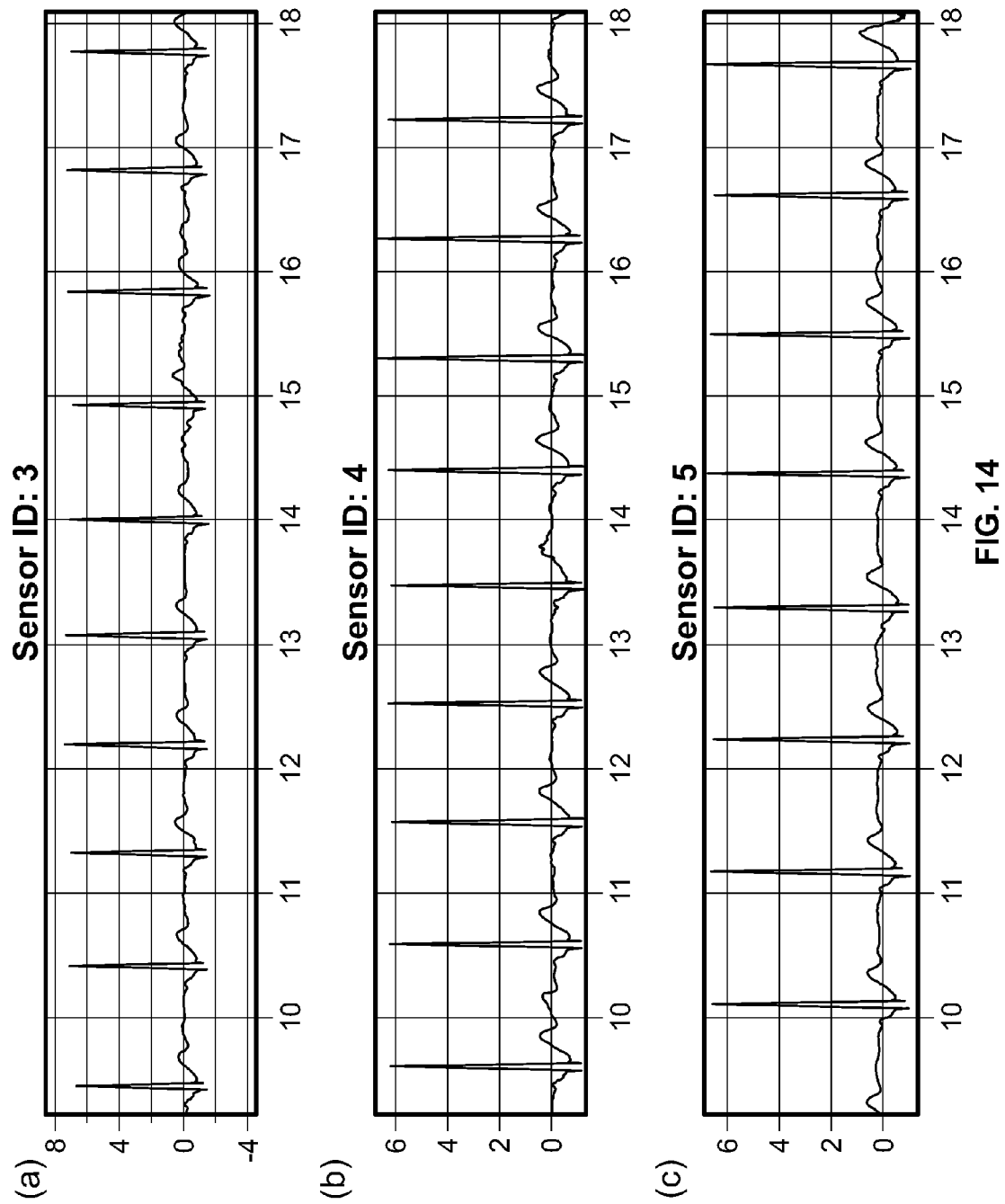
FIG. 14, panels a-c show recorded ECG signals data using electrode serial nos. 3-5 respectively.

Recorded ECG Signals Data using the Electrodes: FIG. 14, panels a-c show recorded ECG signals data using electrode serial nos. 3-5 respectively. Electrodes 3-5 were able to filter out powerline noise, and had similar amplitudes. However, all electrodes were susceptible to movement artifacts.

Figure 11B:
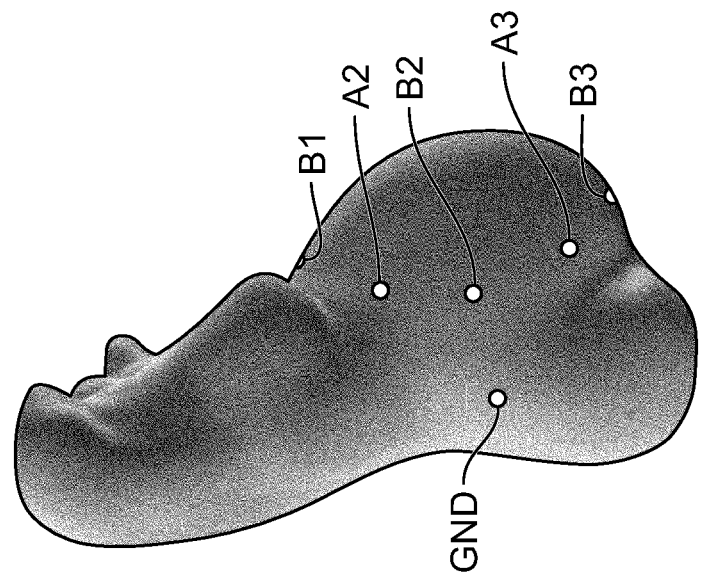
FIG. 11 shows the positions of the ECG sensor pairs on the abdomen of a pregnant woman according to some embodiments of the present invention. Panel a) shows a front view. Panel b) shows a side view.
Figure 11A:
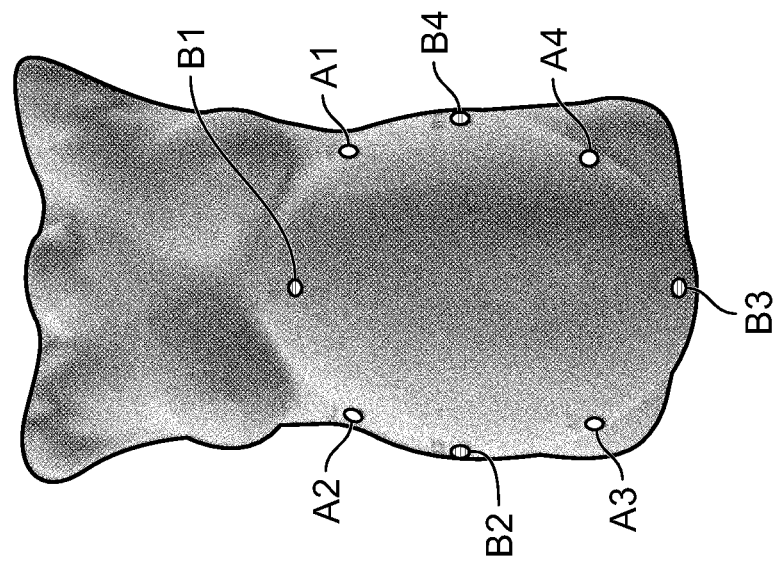
Figure 15:
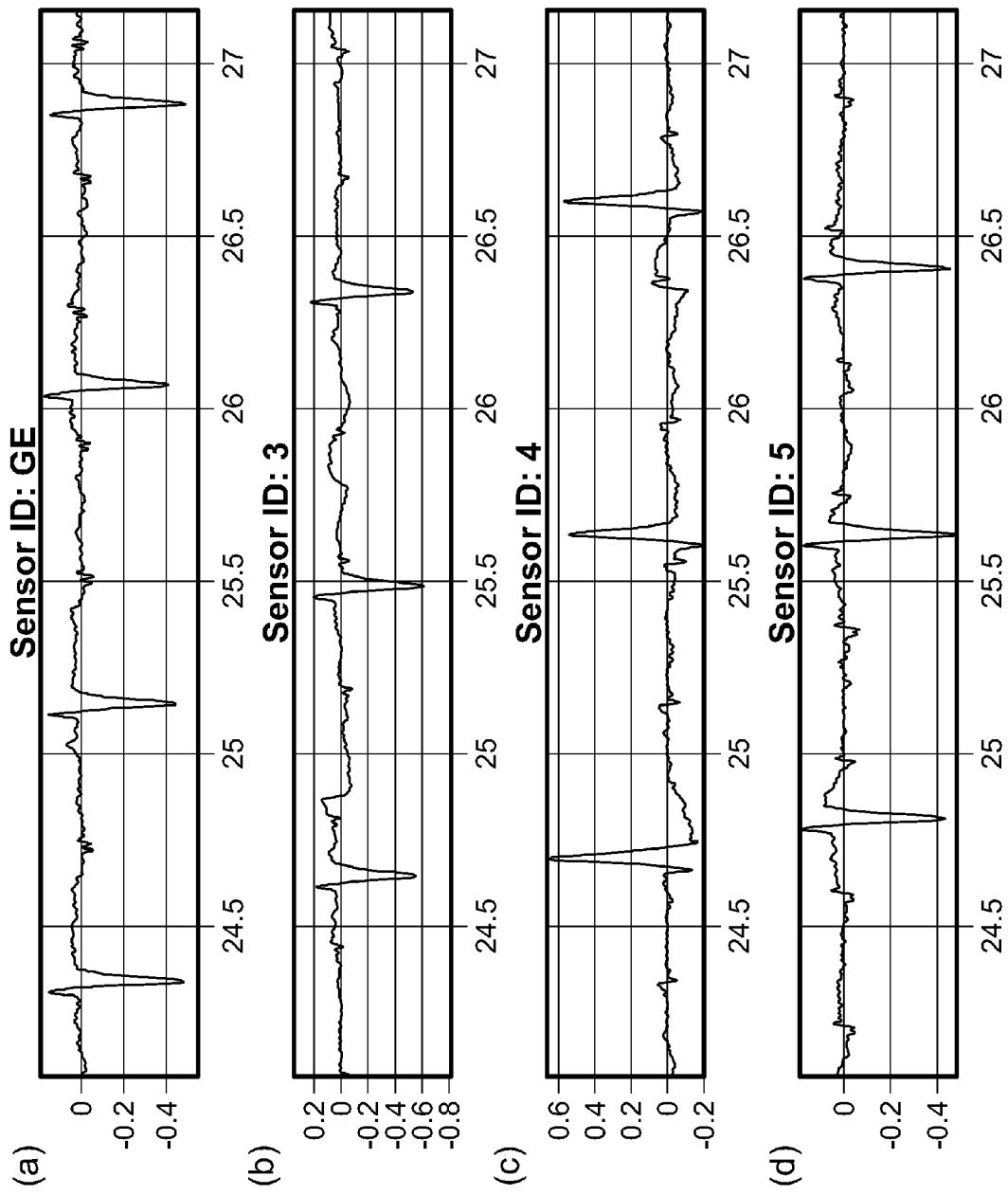
FIG. 15, panels a-d, show the recorded ECG signals data using electrode serial nos. 3-5, and a control wet gel ECG electrode (GE Healthcare), respectively at 25 weeks from a pregnant human subject.
Figure 16:
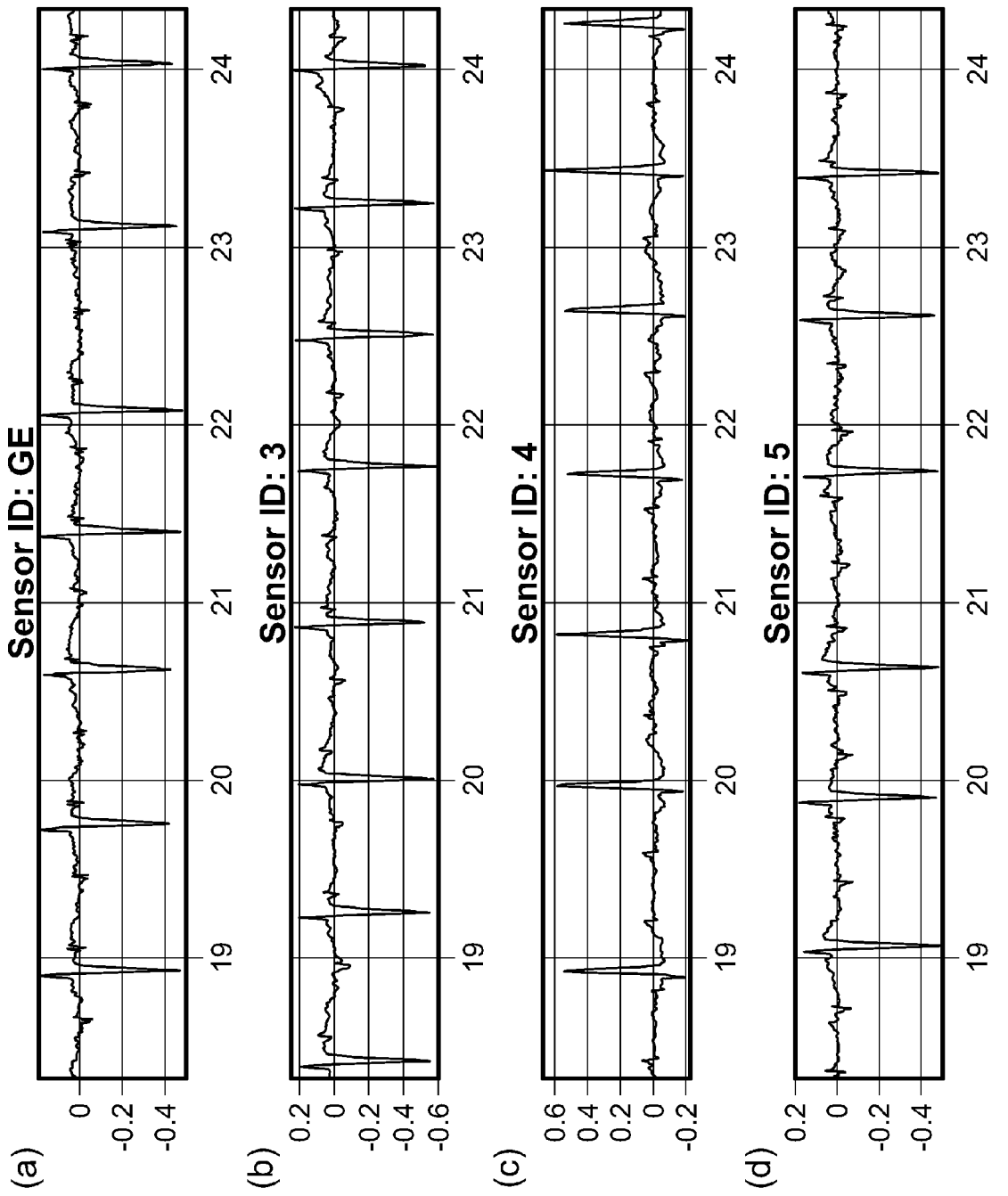
FIG. 16, panels a-d, show the recorded ECG signals data using electrode serial nos. 3-5, and a control wet gel ECG electrode (GE), respectively at 25 weeks from a pregnant human subject.

ECG signal were recorded from two pregnant subjects at week 25 and week 28, using either electrodes 3, 4, 5, and a comparison electrode, using a wet contact electrode, using the electrode position B1-B3 (see FIG. 11 for the electrode position). FIG. 15, panels a-d, and FIG. 16, panels a-d show the recorded ECG signals data using electrode serial nos. 3-5, and the GE comparison electrode respectively at 25 weeks in the two subjects. Fetal ECG were visible in the traces.

Example 2

Measuring Surface Resistivity and Resistance

Figure 17:
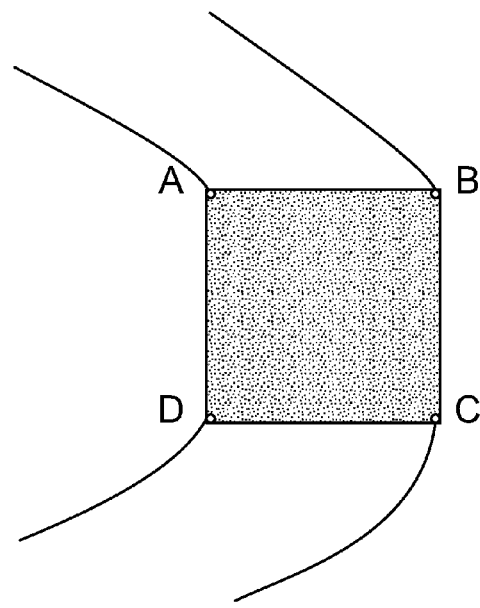
FIG. 17 shows an experimental set up to determine surface resistivity and resistance of an electrically conductive fabric according to some embodiments of the present invention.

FIG. 17 shows an experimental set up to determine surface resistivity and resistance of an electrically conductive fabric according to some embodiments of the present invention. A, B, C, and D are point contact connectors. To measure surface resistivity, current was introduced and recorded according to the following protocol:
1. Connect the sample as described in the background section.
2. Make sure that the current source is running and stable.
3. Inject AB, measure CD;
4. Inject CD, measure AB;
5. Inject BA, measure DC;
6. Inject DC, measure BA;
7. Inject BC, measure DA;
8. Inject DA, measure BC;
9. Inject CB, measure AD;
10. Inject AD, measure CB;

Surface resistance was calculated according to the following:

$$\exp\left(-\frac{\pi R_{AB,CD}}{R_s}\right) + \exp\left(-\frac{\pi R_{BC,AD}}{R_s}\right) = 1$$

$$\text{where } R_{AB,CD}[\Omega] = \frac{V_{DC}}{i_{AB}} = \frac{V_D - V_C}{i_{AB}}$$

is the resistance measured between C and D while introducing current between points A and B; and $i_{AB}$ [A] is the injected current between points A and B; and d [m] is the thickness of the sample; and $\rho$ is the resistivity.

$$\rho = R_s d \ [\Omega \cdot m]$$

$$R_s = \frac{\pi}{\ln 2} \cdot R$$

$$R = R_{vertical} = R_{horizontal}$$

$$R_{vertical} = \frac{(R_{AB,CD} + R_{CD,AB} + R_{BA,DC} + R_{DC,BA})}{2}$$

$$R_{horizontal} = \frac{(R_{BC,DA} + R_{DA,BC} + R_{CB,AD} + R_{AD,CB})}{2}$$

The above protocol was performed using an electrode alone, or an electrode contacting a copper sheet (to measure the resistivity of the electrode-surface interface). Additionally, measurements were obtained after the electrically conductive fabric was stretched either 20%, or 50% in the man direction, or in the direction perpendicular to the main direction.

Example 3

Basic Transfer Function Testing

Figure 18:
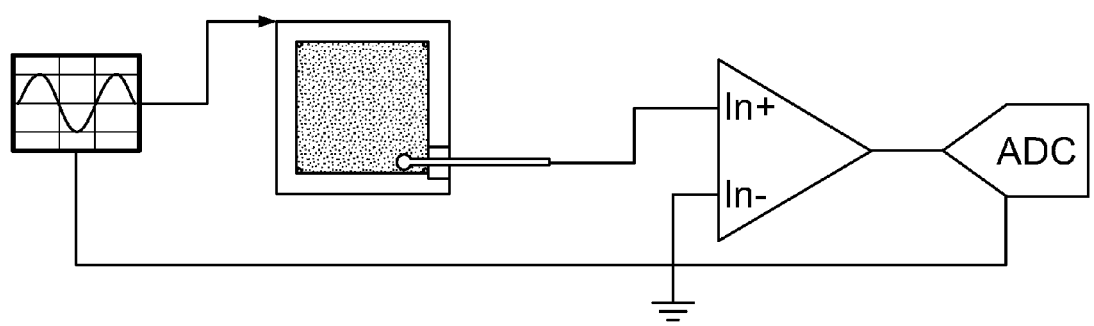
FIG. 18 shows an experimental set up to determine BTFT of an electrically conductive fabric according to some embodiments of the present invention.

An electrode was placed on a copper sheet, such that the cutaneous contact is in contact with the copper sheet, and a 1 kg mass was applied to the electrode. The copper sheet was connected to the positive terminal of a signal generator, the electrode was connected to the positive input of an amplifier, and the other input of the amplifier was connected to ground. FIG. 18 shows the experimental setup described above. A 30 Hz signal was generated by the signal amplifier, and the following parameters were recorded:
1. Time domain:
    a. amplitude-2-amplitude; and
    b. non-zero division; and
    c. time shifts; and
    d. cross correlation; and
    e. correlation coefficient; and
    f. Histogram: Mean, RMS, STD.

2. Frequency domain:
    a. Welch PSD estimation (magnitude); and
    b. Cross coherence; and
    c. Main frequency magnitude; and
    d. Dominant frequencies magnitude; and
    e. SINAD, SNR.

Example 4

Electrophysiological Performance Measurements

The source of the physiological signals detected using the electrodes according to some embodiments of the present invention are located within the body of the pregnant human subject and have extremely low amplitude and low frequency. Without intending to be limited by any particular theory, the physiological signals flow within the body of the pregnant human subject by the movement of ions. The electrodes according to some embodiments of the present invention act as signal transducers, and transduce the movement of ions to the movements of electrons. The skin-electrode interface (SSI) is one determining factor of the electrode's ability to transduce the physiological signals.

Figure 19:
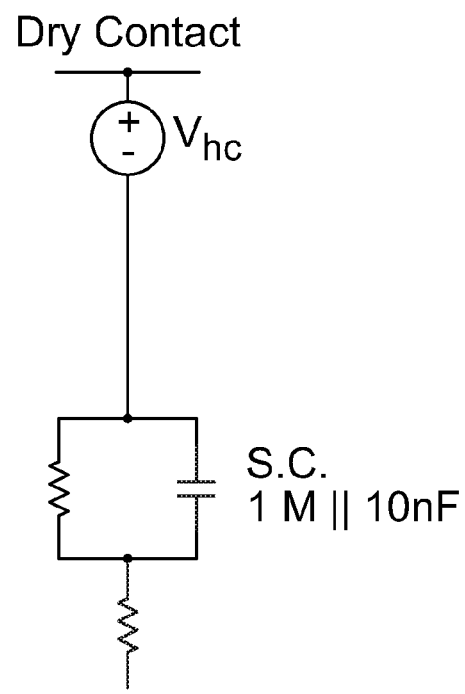
FIG. 19 shows a diagram if a skin-electrode interface equivalent circuit according to some embodiments of the present invention.

The SSI for the electrodes according to some embodiments of the present invention may be modeled by a parallel circuit of an ohmic and capacitive impedance with an additional Warburg resistance (see FIG. 19). Without intending to be limited to any particular theory, both the conductive and the capacitive compartments affect the performance of an electrode according to some embodiments of the present invention. The skin-electrode impedance (SSiM) is equivalent to the impedance of the circuit shown in FIG. 19, and ranges from 10 k$\Omega$ to 100 M$\Omega$. Decreasing the impedance improves the performance of an electrode according to some embodiments of the present invention. Decreasing impedance may be achieved by increasing the surface areas of the cutaneous contact, or by reducing the resistivity of the cutaneous contact. An increase in input impedance and a decrease in input capacitance of the amplifier may also improves the performance of an electrode according to some embodiments of the present invention.

Figure 20:
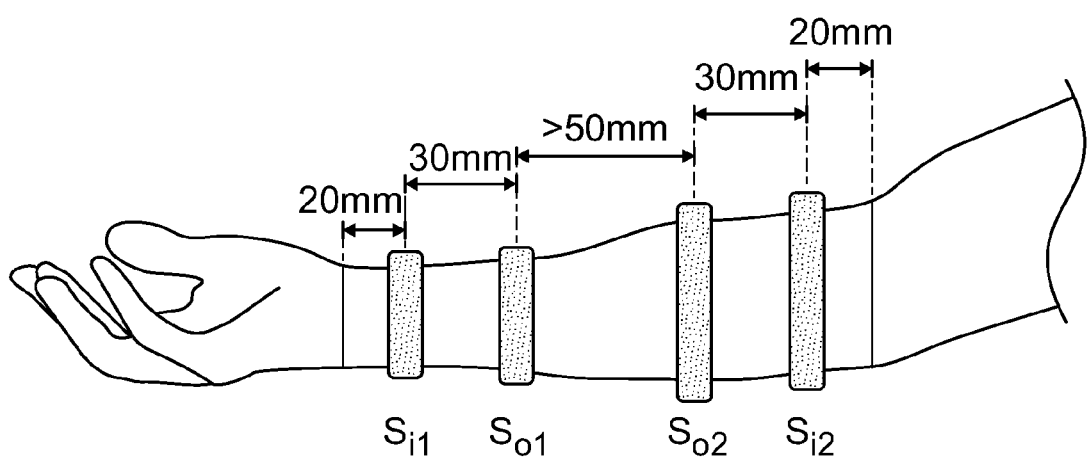
FIG. 20 shows a representation of a test electrode configuration.

In the test protocol, electrodes were applied to the skin of a subject's hand, according to the arrangement shown in FIG. 20. The surface of the hand having first been cleaned. Four VELCRO straps were applied, the pressure of the straps was confirmed to be equal, using a surface pressure sensor. Test electrodes were then inserted under the straps. The pressure that the electrodes contact the skin was confirmed to be equal, using a surface pressure sensor. Impedance was measured as follows:
    2-wire: measure the 2wire resistance between the $S_i$ electrodes and the $S_o$ electrodes (2 measurements).
    4-wire: use the $S_i$ electrodes as the injectors and the $S_o$ electrodes as the measurers. Measure the resistance (1 measurement).
    Capacitance measurement: measure the 2wire capacitance between the $S_i$ electrodes and the $S_o$ electrodes (2 measurements).

A 150 m $V_{pp}$ sine wave was applied to the $S_i$ electrodes, and the voltage developed at the $S_o$ electrodes was recorded using a BioPac amplifier, sold by BioPac systems Inc. Recordings were obtained using a sine wave of the following frequencies: 0.1, 1, 5, 10, 15, 20, 25, 30, 35, 40, 45, 50, 55, 60, 70, 80, 90, Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. An electrode configured to detect fetal electrocardiogram signals, the electrode comprising:
   a. a cutaneous contact for sensing fetal electrocardiogram signals from a pregnant human subject, the cutaneous contact including an electrically conductive fabric;
   b. an elastomeric dome underlying the cutaneous contact, the elastomeric dome configured to deform when placed on an abdomen of the pregnant human subject so as to cause the cutaneous contact to be in electrical communication with skin of the pregnant human subject;
   c. a connector in electrical contact with the cutaneous contact for connection to a lead wire; and
   d. a substructure for attachment to a human pregnant subject.

2. The electrode of claim 1, wherein the cutaneous contact is configured to have skin-electrode impedance of greater than 150 k$\Omega$.

3. The electrode of claim 1, wherein the cutaneous contact is configured to have skin-electrode impedance of less than 150 k$\Omega$.

4. The electrode of claim 1, wherein the cutaneous contact is configured to have skin-electrode impedance of between 5 to 150 k$\Omega$.

5. The electrode of claim 1, wherein the elastomeric dome is configured to deform when placed on the abdomen of the pregnant human subject to create a skin-electrode impedance of less than 150 k$\Omega$.

6. The electrode of claim 1, wherein the elastomeric dome is configured to deform when placed on the abdomen of the pregnant human subject to create a skin-electrode impedance of between 5 to 150 k$\Omega$.

7. The electrode of claim 1, wherein the cutaneous contact is configured to have a surface resistance of less than 1 $\Omega$/square.

8. The electrode of claim 1, wherein the cutaneous contact is configured to have a surface resistance between 0.01 and 1 $\Omega$/square.

9. The electrode of claim 1, wherein the signal to noise ratio of the fetal electrocardiogram signals is between −20 dB and 50 dB.

10. The electrode of claim 1, wherein the signal to noise ratio of the fetal electrocardiogram signals is between 0 dB and 50 dB.

11. The electrode of claim 1, wherein the electrically conductive fabric has a skin-electrode impedance of less than 150 k$\Omega$.

12. The electrode of claim 1, wherein the electrically conductive fabric has a skin-electrode impedance of between 5 to 150 k$\Omega$.

13. The electrode of claim 1, wherein the surface of the electrically conductive fabric that forms the cutaneous contact is configured to have a surface resistance of less than 1 $\Omega$/square.

14. A garment, comprising:
   a. at least one pair of electrodes,
   wherein the at least one pair of electrodes are configured, when the garment is worn by the pregnant human subject, so that the individual electrodes of the at least one electrode pair encircle the uterus of the pregnant human subject, and
   wherein the individual electrodes of the at least one electrode pair comprise:
      1. a cutaneous contact for sensing fetal electrocardiogram signals from a pregnant human subject, the cutaneous contact including an electrically conductive fabric;
      2. an elastomeric dome underlying the cutaneous contact, the elastomeric dome configured to deform when placed on an abdomen of the pregnant human subject so as to cause the cutaneous contact to be in electrical communication with skin of the pregnant human subject;
      3. a connector in electrical contact with the cutaneous contact for connection to a lead wire; and
      4. a substructure for attachment to a human pregnant subject,
   wherein cardiac electrical activity data is recorded from the at least one sensor pair.

* * * * *